United States Patent [19]

Sewell, Jr.

[11] Patent Number: 5,152,772
[45] Date of Patent: Oct. 6, 1992

[54] SPHINCTEROTOMY CATHETER AND METHOD

[76] Inventor: Frank Sewell, Jr., 1413 N. Elm. Henderson, Ky. 42420

[21] Appl. No.: 728,178

[22] Filed: Jul. 10, 1991

[51] Int. Cl.⁵ .............................................. A61B 17/32
[52] U.S. Cl. .................................... 606/159; 604/22; 606/192; 606/170
[58] Field of Search ............................ 604/22, 51–53, 604/96. 101, 104. 264, 280, 282; 606/127, 159–161, 167, 170, 171, 179, 191–194

[56] References Cited

U.S. PATENT DOCUMENTS

| 518.600 | 4/1894 | Hallman | 606/170 |
|---|---|---|---|
| 2.715.899 | 8/1955 | MacLean | 604/22 X |
| 3.108.593 | 10/1963 | Glassman . | |
| 4.271.839 | 6/1981 | Fogarty et al. . | |
| 4.295.464 | 10/1981 | Shihata | 606/127 |
| 4.484.579 | 11/1984 | Meno et al. . | |
| 4.561.439 | 12/1985 | Bishop et al. . | |
| 4.627.837 | 12/1986 | Gonzalo | 604/101 |
| 4.690.138 | 9/1987 | Heydon | 128/207.15 |
| 4.696.668 | 9/1987 | Wilcox | 604/28 |
| 4.705.041 | 11/1987 | Kim . | |
| 4.734.094 | 3/1988 | Jacob et al. | 604/284 |
| 4.781.677 | 11/1988 | Wilcox | 604/28 |
| 4.798.586 | 1/1989 | Stevens | 604/96 |
| 4.811.735 | 3/1989 | Nash et al. . | |
| 4.911.163 | 3/1990 | Fina | 606/127 |
| 5.024.617 | 6/1991 | Karpiel | 606/47 |
| 5.035.696 | 7/1991 | Rydell | 606/47 |
| 5.053.044 | 10/1991 | Mueller et al. | 606/159 |
| 5.078.722 | 1/1992 | Stevens | 606/159 |

FOREIGN PATENT DOCUMENTS

2804015 8/1979 Fed. Rep. of Germany ........ 604/22

OTHER PUBLICATIONS

Flexiflo ® Gastrostomy Tube Sales brochure, Ross Laboratories, 1989.
Duodenofiberscope sales brochure, Olympus, pp. 1,3,4, and 9, undated.

*Primary Examiner*—C. Fred Rosenbaum
*Assistant Examiner*—Adam J. Cermak
*Attorney, Agent, or Firm*—Baker & Daniels

[57] ABSTRACT

Method for performing a laparoscopic sphincterotomy involving the steps of positioning a catheter within the duodenum by inserting the distal end of the catheter into the common bile duct and threading the distal end of the catheter into the duodenum, positioning the cutting mechanism of the catheter against the sphincter of Oddi, cutting the sphincter of Oddi with the cutting mechanism, and removing the catheter. The invention also includes a surgical catheter to be used to perform such a sphincterotomy. The catheter includes an elongated longitudinal channel. two separate balloons located at the distal end of the catheter, and a cutting mechanism extendable from the catheter between the two balloons. The catheter also includes a radial mark at the operative end of the catheter that lies in the same radial position with respect to the longitudinal channel of the catheter as the cutting mechanism. The catheter and method disclosed allow a surgeon to perform a laparoscopic sphincterotomy that is safe and efficient, and allows a patient's gall stones, gall bladder disease, common duct stone, and inflammation of the ampulla to be treated during a single procedure.

13 Claims, 8 Drawing Sheets

SPHINCTEROTOMY CATHETER AND METHOD

FIELD OF THE INVENTION

This invention relates to a medical device used in laparoscopic surgery, and, in particular, to a catheter and a method used for the performance of a laparoscopic sphincterotomy.

BACKGROUND OF THE INVENTION

The common bile duct is about eight (8) to ten (10) millimeters in diameter and may dilate if obstructed by biliary stones or other foreign matter. The common bile duct tapers to a diameter of one (1) millimeter as it enters the wall of the duodenum. In this area, smooth muscle fibers surround both the common bile duct and the pancreatic duct which enter the duodenum from the side. These fibers are collectively called the sphincter of Oddi and are responsible for the tapering of the common bile duct as it transverses the duodenal wall. If the common bile duct joins to the pancreatic duct within the duodenal wall, the resulting structure is called the ampulla of Vater. This small protrusion can frequently be seen from the inside of the duodenum, but on some patients, it is too small for visualization.

If the sphincter of Oddi impedes the passage of stones in the common bile duct, it is cut in an operation called a sphincterotomy. A sphincterotomy often involves opening the duodenum, locating the small papilla called the ampulla of Vater, and incising the fibers at a particular radial position to avoid injury to the pancreatic duct. It is a difficult procedure, and the possibility of complications from either pancreatitis from an injury to the pancreatic duct or a fistula from the duodenum or common duct are very serious. An alternate procedure that can be performed lieu of a sphincterotomy is to anastomose the common duct to the duodenum or other small bowel. This is also a difficult procedure from which there is also a possibility of a fistula if the anastomosis leaks.

A sphincterotomy may alternatively be performed endoscopically through a side-viewing gastroduodenoscope. This type of sphincterotomy was first performed in 1974 and has become the method of choice. When performed endoscopically, general anesthesia is not needed and the duodenum is not opened. This method has been recommended for use after laparoscopic cholangiograms reveal the presence of common duct stones. The patient is allowed several days to recover from a laparoscopic cholecystectomy before being endoscoped via a side-viewing gastroduodenoscope. After retrograde cholangiopancreatography and X-ray pictures of the biliary and pancreatic ducts are completed, the sphincterotomy is performed. Large common duct stones are retrieved using stone baskets or other instruments. Small stones are left to be washed out of the common duct into the duodenum after the sphincterotomy is complete. In most instances, a general surgeon performs the laparoscopic cholecystectomy and a gastroenterologist treats the common duct stones. The patient undergoes two major procedures and two sets of multiple X-rays.

Representative of the type of surgical equipment used for endoscopically completing a sphincterotomy is the Olympus Endoscopy System available from Olympus Corporation in Lake Success, N.Y. To perform the incision in a sphincterotomy, a papillotomy knife (such as Olympus models KD-4Q, KD-5Q, and KD-6Q) is used in conjuction with a fiberscope (such as the Olympus JF-10 ERCF Duodenofiberscope). Through the limited vision provided through the laparoscopic ports, the papillotomy knife catheter is positioned and the cutting edge is moved by controls made available to the surgeon to incise the fibers. Special care must be taken with such a procedure to properly position the cutting edge and to maintain that position until the incision is complete.

Several catheters are available for the removal or destruction of calculi or stones within the body. U.S. Pat. No. 4,911,163, discloses a device used for the removal of calculi from the ureter; U.S. Pat. No. 4,627,837, discloses a device used for the removal of stones from the common duct; and U.S. Pat. No. 4,561,439, discloses a device used for the removal of gall stones. Each of these patents disclose catheters in which balloons are at or near the distal end of the device and are used to perform their respective functions. Generally, the balloons are used to hold the stones while they are dragged out of the appropriate duct. U.S. Pat. No. 4,627,837 uses one balloon at the distal end of the catheter to anchor the catheter at the sphincter of Oddi and a second balloon near the distal end of the catheter to catch and remove the stones located in the common bile duct near the sphincter of Oddi. U.S. Pat. No. 3,108,593 discloses a catheter in which cages or bobbins are positioned from the distal end of the catheter and which dislodges and entraps bile duct stones, but which requires that incisions be made in the duodenum and the common bile duct.

The device disclosed in U.S. Pat. No. 4,811,735 is used to destroy stones through the use of rotating blades at the distal end of the catheter. U.S. Pat. Nos. 4,696,668 and 4,781,677 disclose a catheter that can be utilized to destroy stones by injecting a dissolving agent into the gall bladder after positioning the two inflated balloons near the distal end of the catheter within the common bile duct. Similar techniques are employed in the device disclosed in U.S. Pat. No. 4,734,094 wherein a contrast fluid can be injected in between the ballons at the end of the catheter for X-ray cholangiography.

Several other ballooned catheters exist for a variety of purposes. The catheter disclosed in U.S. Pat. No. 4,271,839 is used for the dilation of occluded blood vessels. Commercially available products include the Flexiflo(R) Gastrostomy Tube available from Ross Laboratories, Columbus, Ohio.

U.S. Pat. No. 4,705,041 discloses a catheter and a method used to dilate the sphincter of Oddi during open surgery. The catheter does not include a balloon, but does include an expandable tip used to position the distal end of the catheter in preparation for the placement of tube-like dilators over the catheter.

A multi-functional catheter used to complete a commissurotomy is disclosed in U.S. Pat. No. 4,484,579. This device comprises balloons at the distal end of the catheter as well as cutting edges located between the balloons such that, once the balloons are positioned, the cutting edges are able to separate fused heart valves.

To endoscopically perform a sphincterotomy in the most efficient manner requires a catheter that can be inserted into the common bile duct, threaded into the duodenum through the sphincter of Oddi, radially positioned within the ampulla, and then make the necessary incision. None of the above references can be used in this manner.

OBJECTS OF THE INVENTION

One object of the invention is to provide a device and method whereby a sphincterotomy may be performed laparoscopically.

It is another object of the invention to allow a patient's gall stones, gall bladder disease, common duct stone, and inflammation of the ampulla to be treated during a single procedure.

SUMMARY OF THE INVENTION

The invention includes a method for performing a laparoscopic sphincterotomy comprising the steps of positioning a catheter within the duodenum by inserting the distal end of the catheter into the common bile duct and threading the distal end of the catheter into the duodenum, positioning the cutting means of the catheter against the sphincter of Oddi, cutting the sphincter of Oddi with the cutting means, and removing the catheter. The invention also includes a surgical catheter to be used to perform such a sphincterotomy. The catheter includes an elongated longitudinal channel, two separate balloons located at the distal end of the catheter, and a cutting means extendable from the catheter between the two balloons. The catheter also includes a radial mark at the operative end of the catheter that lies in the same radial position with respect to the longitudinal channel of the catheter as the cutting means. The catheter and method disclosed allow a surgeon to perform a laparoscopic sphincterotomy that is safe and efficient, and allows a patient's gall stones, gall bladder disease, common duct stone, and inflammation of the ampulla to be treated during a single procedure.

DETAILED DESCRIPTION

Figure 1:
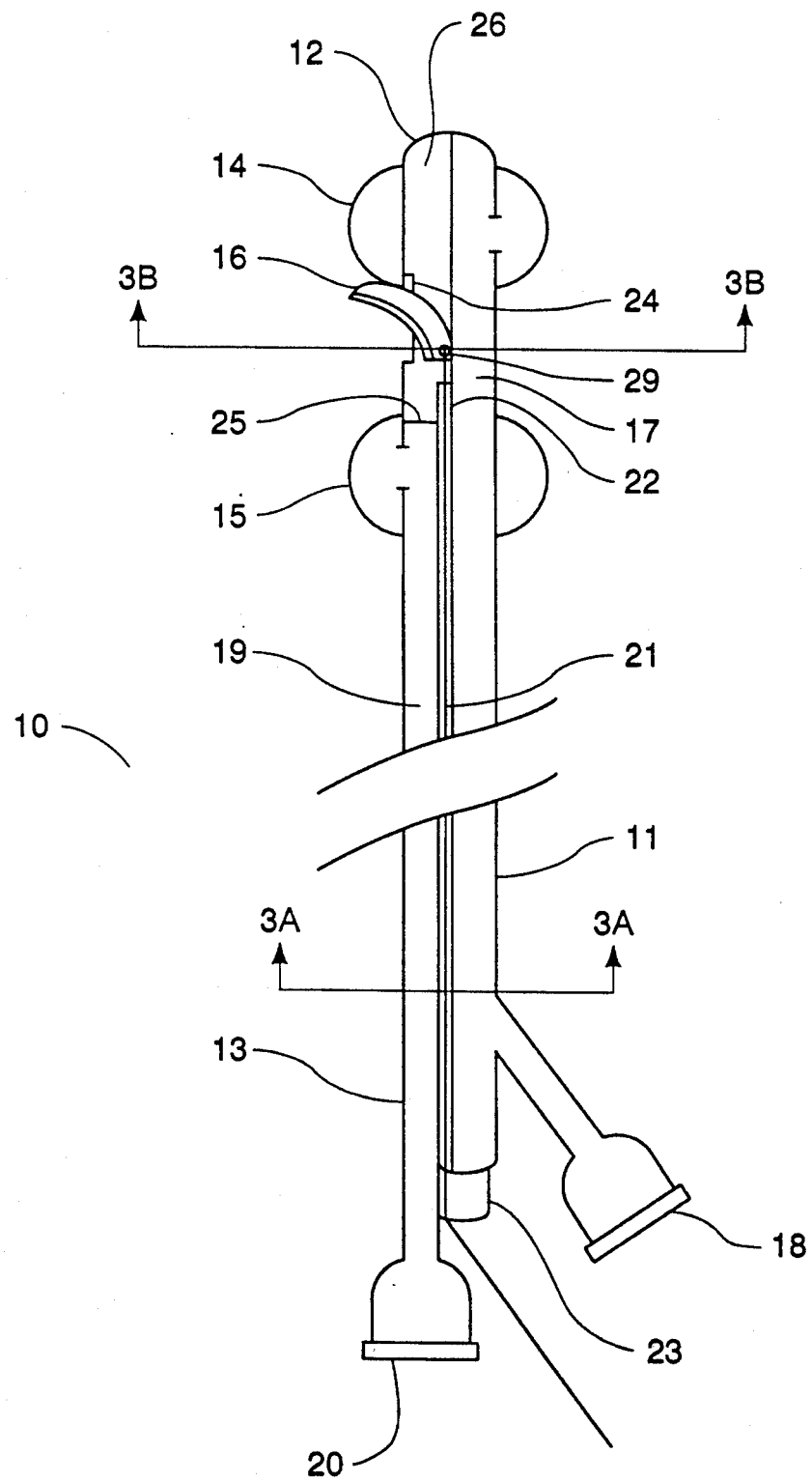
FIG. 1 shows a longitudinal cross-sectional view of the sphincterotomy catheter according to the present invention in which both balloons are inflated and in which the cutting means is in its extended position.

Referring now to FIG. 1, there is shown a longitudinal cross-sectional view of the catheter according to the present invention. Catheter 10 includes an elongated channel 11 having distal end 12 and operative end 13. Near distal end 12 of catheter 10 are two separate inflatable means 14 and 15 with cutting means 16 located between first inflatable means 14 and second inflatable means 15. First balloon 14 is inflated by introducing a gas or a fluid to first port 18 which flows through first lumen 17 into first balloon 14. Similarly, second balloon 15 is inflated by introducing a gas or a fluid to second port 20 which flows through second lumen 19 and into second balloon 15. Second lumen 19 is terminated by stop 25 beyond which is cutting channel 26 which cannot be filled by a gas or a fluid introduced to either first 18 or second 20 ports. Cutting means 16 is slidably affixed to attachment means (see items 27, 28 in FIGS. 3B and 4) by axle 29 about which cutting means 16 is able to pivot. Also affixed to cutting means 16 is bias means 21 which biases cutting means 16 toward a retracted position. Bias means 21 is operatively connected to blade 16 at one end and to screw mechanism 23 at its other end, and resides within third lumen 22. When radially extended, blade 16 extends beyond the outer surface of channel 11 and cutting channel 26 through slot 24.

Figure 2:
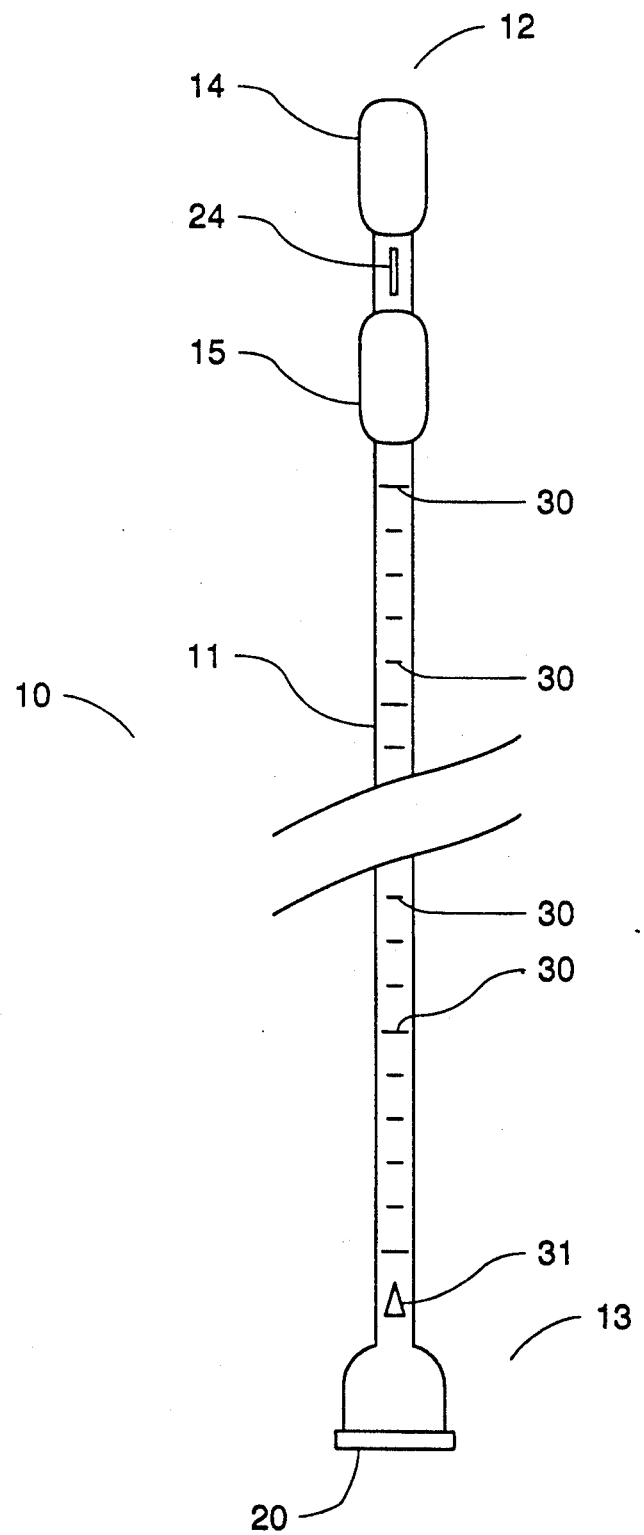
FIG. 2 shows a top view of the catheter of FIG. 1 in which both balloons are deflated and the blade is in its retracted position.

In FIG. 2, there is shown a top view of the catheter of the present invention in which both first 14 and second 15 inflatable means are deflated and in which blade 16 is in its retracted position. Present on channel 11 are measuring markings 30 which provide a means of measuring the depth to which catheter 10 is inserted with respect to an incision. Radial mark 31 at operative end 13 of catheter 10 is located such that radial mark 31 lies in the same radial position with respect to longitudinal channel 11 as cutting means 16.

Figure 3A:
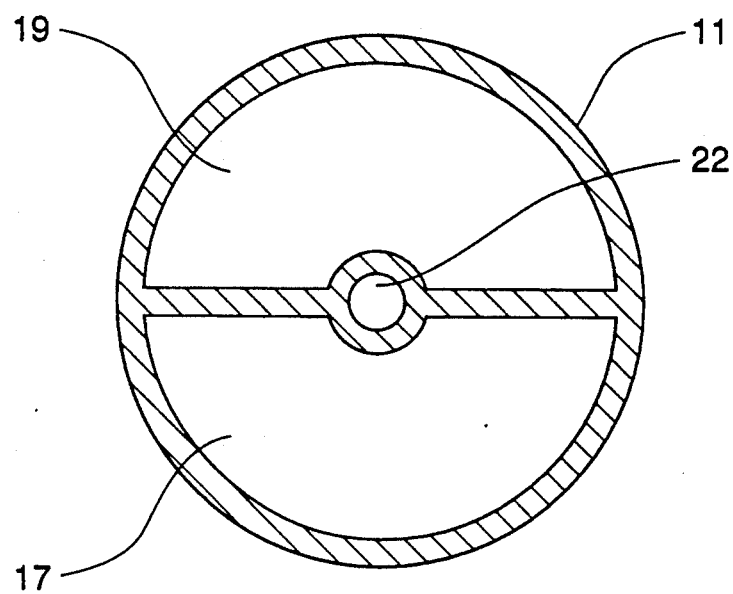
FIG. 3A shows a cross-sectional view of the catheter of FIG. 1.
Figure 3B:
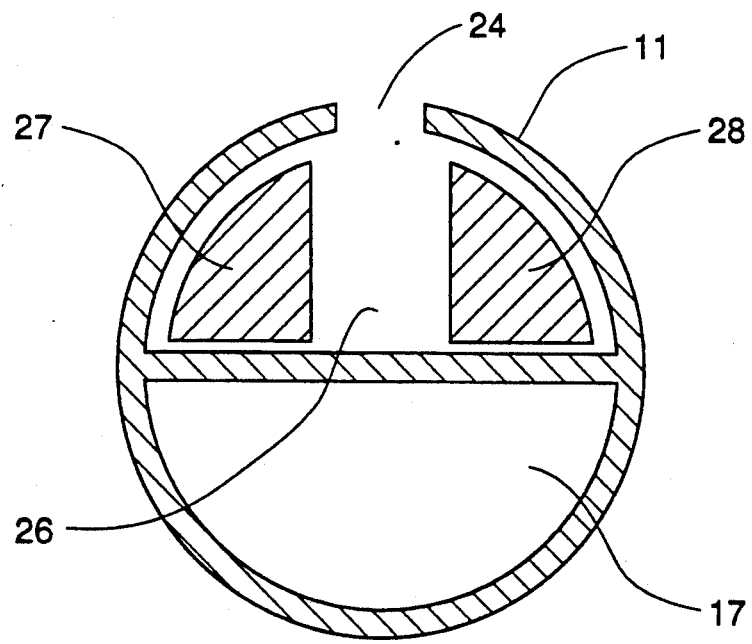
FIG. 3B shows a cross-sectional view of the catheter of FIG. 1 at the portion of the catheter in which the cutting means is secured.
Figure 4:
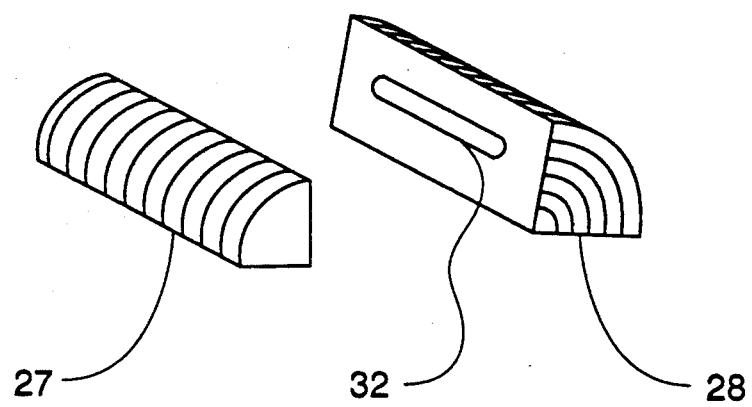
FIG. 4 shows a perspective view of the attachment means to which the cutting means of the catheter is affixed to the catheter of FIG. 1.

Referring now to FIG. 3A, there is shown a cross-sectional view of channel 11 near operative end 13. Third lumen 22 which holds bias means 21 is located in the center of channel 11. First and second lumens 17 and 19 are symmetrically disposed about third lumen 22. FIG. 3B shows a cross-sectional view of channel 11 closer to distal end 12 of channel 11 and at the point about which axle 29 pivots. Means 27, 28 for attaching axle 29 to channel 11 resides within cutting channel 26. A perspective view of attachment means 27, 28 is shown in FIG. 4. Axle 29 is longitudinally slidable within slots 32 of attachment means 27, 28.

Figure 5:
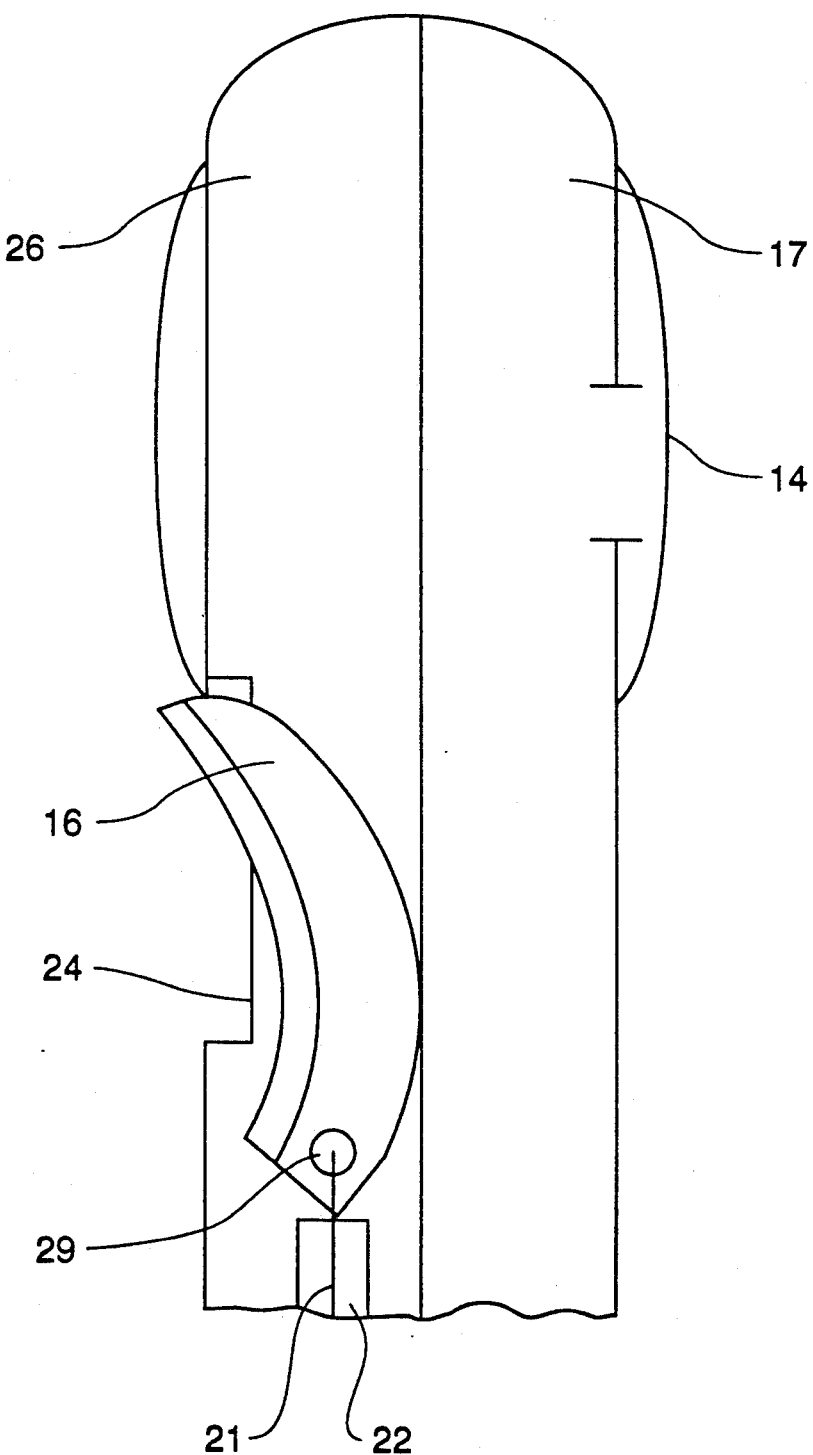
FIG. 5 shows a longitudinal cross-sectional view of the distal portion of the catheter of FIG. 1 in which the cutting means is in its retracted position.
Figure 6:
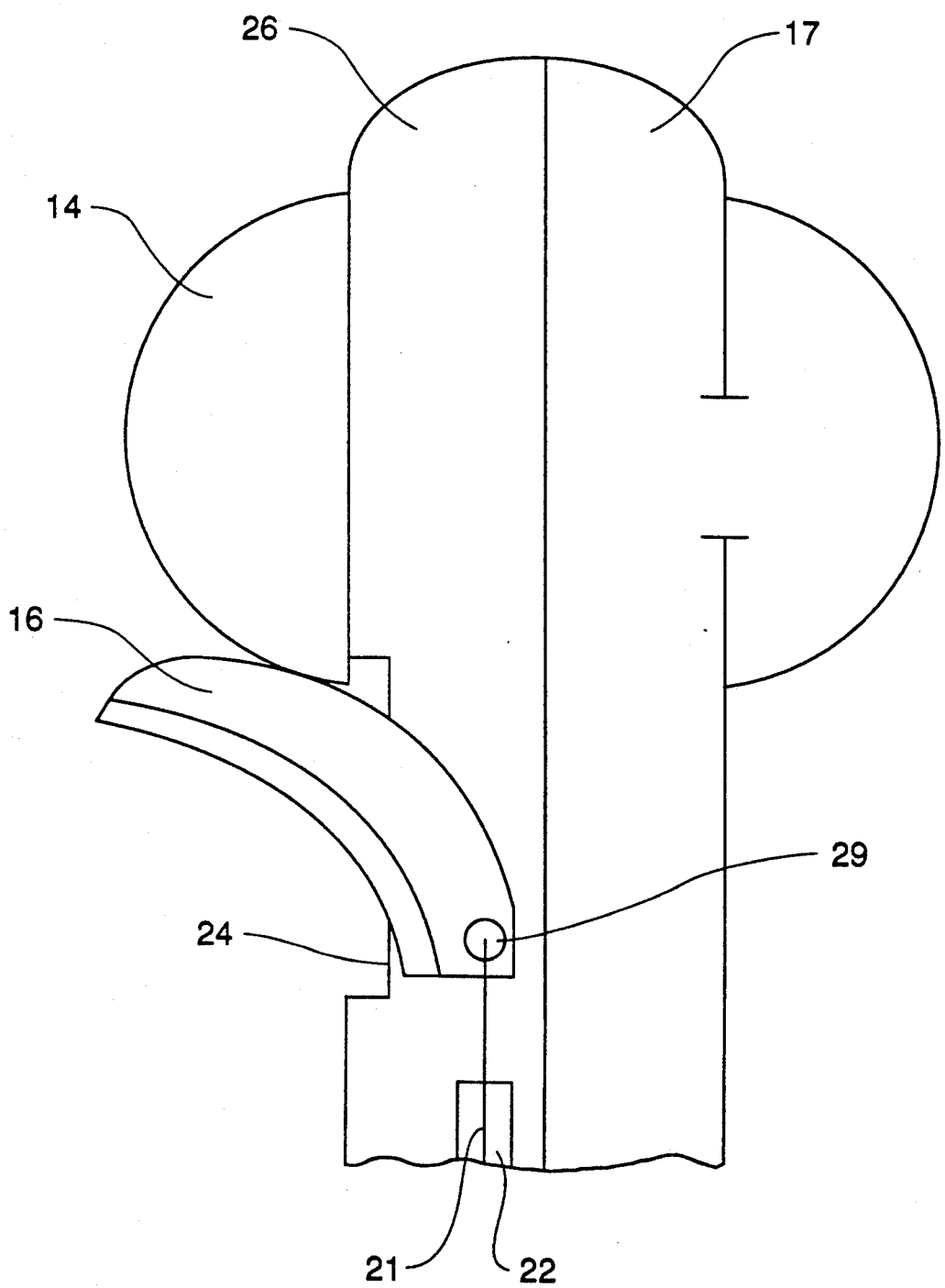
FIG. 6 shows a longitudinal cross-sectional view of the distal portion of the catheter of FIG. 1 in which the first inflatable means is inflated and the cutting means is in its extended position.

FIGS. 5 and 6 show cross-sectional views of distal end 12 of catheter 10 in which first balloon 14 is inflated and deflated, respectively. First ballon 14 is located such that its inflation biases the cutting means 16 toward the extended position.

Figure 7:
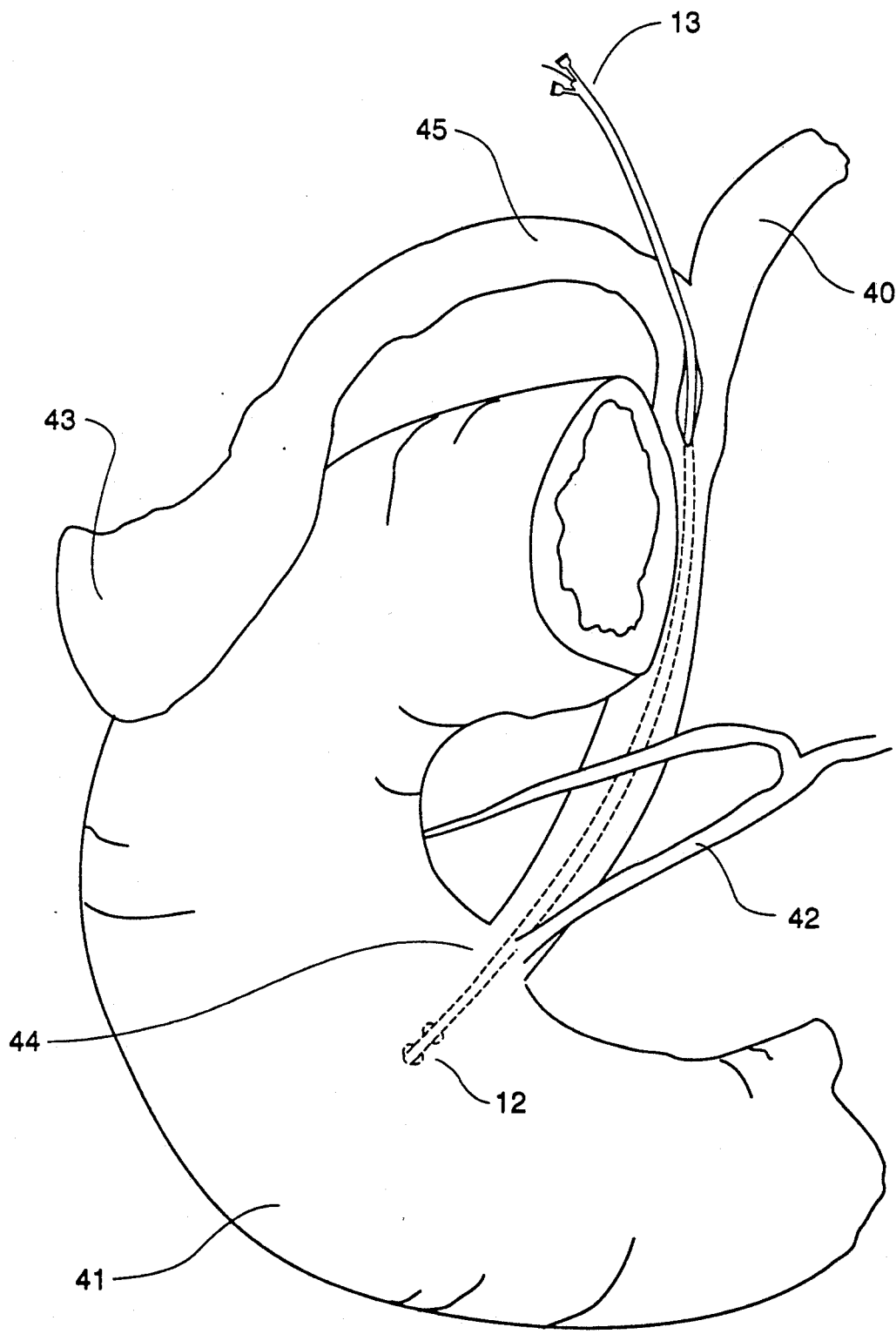
FIG. 7 shows a perspective view of the catheter of FIG. 1 as it is inserted into the cystic duct and into the duodenum.
Figure 8:
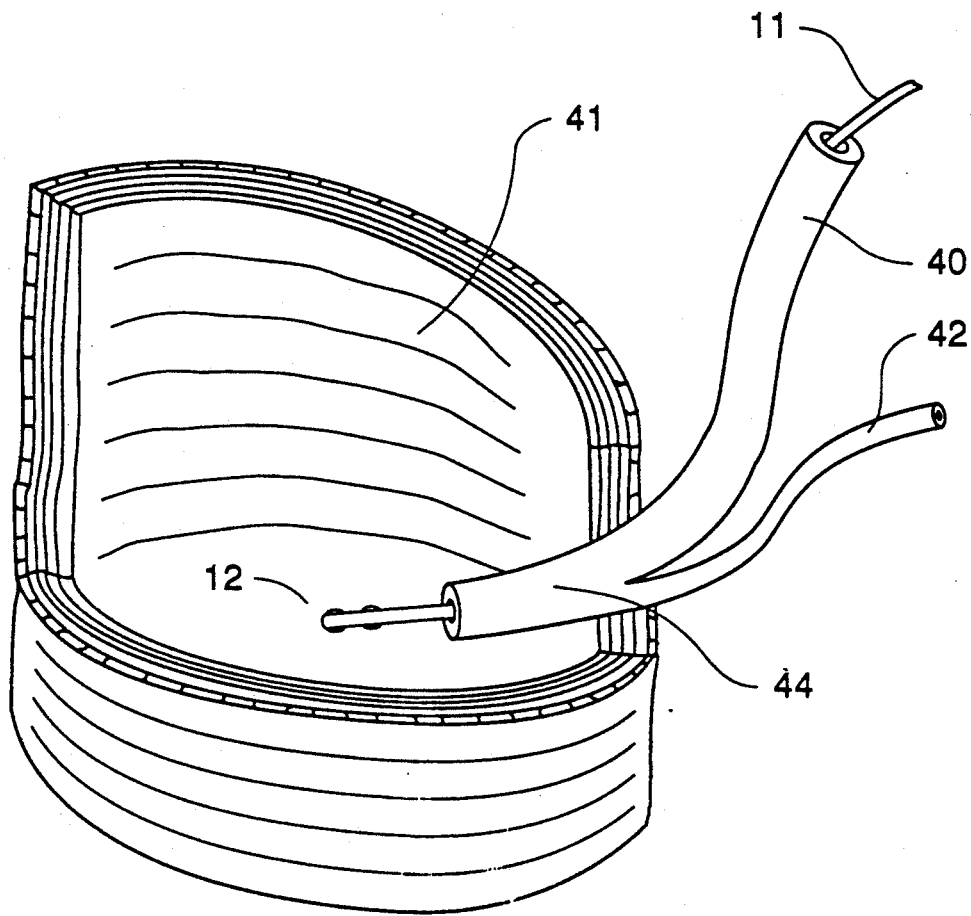
FIG. 8 shows a perspective view of the catheter of FIG. 1 as it extends through the sphincter of Oddi into the duodenum.

Referring now to FIG. 7, there is shown a perspective view of the catheter of the present invention as it is inserted through an incision in common bile duct 40 and threaded through duodenum 41. Distal end 12 is inside duodenum 41 while operative end 13 remains outside common bile duct 40 and may extend outside the patient through a laparoscopic trocar. To permit the flow of small gall stones from gall bladder 43 to the intestinal system, stones need to pass through sphincter of Oddi 44. However, sphincter of Oddi 44, as shown in FIG. 8, is very narrow. Catheter 10 allows a surgeon to laparoscopically cut a small incision in sphincter of Oddi 44 without cutting pancreatic duct 42.

A sphincterotomy may be determined to be necessary when a cholangiogram taken during a cholecystectomy reveals that stones are occluding the sphincter of Oddi. During the cholecystectomy, an incision will have been made in the cystic duct. Catheter 10 may either be inserted in this incision or in a separate incision made in the common bile duct.

In the first step of the laparoscopic surgical procedure, distal end 12 of catheter 10 is inserted through the common bile duct 40 and threaded through sphincter of Oddi 44 until both first 14 and second 15 inflatable means have passed sphincter of Oddi 44 and are within duodenum 41. Second inflatable means 15 is filled with air through second port 20 and catheter 10 is retracted until second balloon 15 abuts sphincter of Oddi 44. Through the laparoscopic camera, the surgeon may note measuring markings 30 denoting the extent to which catheter 10 is inserted into common bile duct 40. The surgeon then rotates catheter 10 so blade 16 is not facing main pancreatic duct 42 by noting the position of radial mark 31. Second balloon 15 is then deflated by allowing the air to exit from second port 20. Then, first ballon 14 is filled with saline, extending cutting means 16 through slot 24. Using screw mechanism 23, the extent to which cutting means 16 is extended is controlled. At this point, cutting means 16 is in the middle of duodenum 41. Next, the surgeon retracts catheter 10 so that blade 16 touches sphincter of Oddi 44 and notes measuring markings 30 at the incision in common bile duct 40 by looking through the laparoscopic camera. Then, the sphincterotomy incision is made by retracting catheter 10 approximately one (1) centimeter.

It will be appreciated by those of skill in the art that the above described procedure results in a safe procedure and may be performed during either laparoscopic or open surgery. The sphincter of Oddi may be cut without cutting the pancreatic duct and without creating a long incision in the abdomen of the patient. The procedure is also efficient in that only one instrument is required to perform the operation.

To remove the catheter, blade 16 is then retracted by the screw mechanism and first balloon 14 is deflated, allowing blade 16 to reside completely within cutting channel 26. The catheter may then be withdrawn until distal end 12 of catheter 10 is outside of common bile duct 40.

It will be appreciated by those of skill in the art that catheter 10 may also be used to achieve tamponade and dilate the sphincter of Oddi. After performance of the sphincterotomy (after retracting the blade but before withdrawing catheter 10), catheter 10 is inserted further into duodenum 41 until second 15 inflatable means is directly in sphincter 44. Inflating and holding second balloon 15 in place for a sufficient time (about three to four minutes) will achieve the desire results. Then, second balloon 15 is deflated and catheter 10 is withdrawn.

I claim:

1. A surgical catheter comprising:
an elongated longitudinal channel having a distal end and an operative end,
a first inflatable means located at the distal end of the catheter,
a second inflatable means, separate from the first inflatable means, located at the distal end of the catheter,
a cutting means radially extendable from the catheter between the first and second inflatable means, and
a radial mark at the operative end of the catheter, such that the radial mark lies in the same radial position with respect to the longitudinal channel of the catheter as the cutting means.

2. The catheter of claim 1 wherein the first inflatable means engages the cutting means when it is inflated.

3. The catheter of claim 1 wherein each inflatable means comprises:
a balloon at the distal end of the catheter,
a port at the operative end of the catheter, and
a lumen within the channel,
the lumen being in communication with the balloon and the port.

4. The catheter of claim 1 wherein the cutting means comprises a blade, the blade being pivotable with respect to the channel.

5. The catheter of claim 1 further comprising a means for adjusting the extent to which the cutting means extends from the catheter.

6. The catheter of claim 5 wherein the means for adjusting comprises a bias means connected to the cutting means at one end, the other end being at the operative end of the catheter, and biasing the cutting means toward a retracted position.

7. The catheter of claim 1 further comprising multiple measuring markings along the exterior of the catheter.

8. A method for performing a sphincterotomy comprising the steps of:
positioning a catheter having distal and operative ends, the catheter comprising a cutting means, within the duodenum by inserting the distal end of the catheter into the common bile duct and thereafter threading the distal end of the catheter into the duodenum,
positioning the cutting means of the catheter against the sphincter of Oddi,
cutting the sphincter of Oddi with the cutting means, and
removing the catheter.

9. The method of claim 8 wherein the surgical catheter of claim 1 is used to perform the sphincterotomy.

10. The method of claim 8 further comprising, before cutting the sphincter of Oddi with the cutting means, the steps of:
providing the catheter with a balloon adjacent the cutting means and on the operative side of the cutting means,
inflating the balloon,
retracting the catheter from the duodenum until the balloon abuts the sphincter of Oddi, and
deflating the balloon.

11. The method of claim 8 further comprising, before cutting the sphincter of Oddi with the cutting means, the step of rotating the catheter so that the cutting means is not facing the main pancreatic duct.

12. The method of claim 8 further comprising, before removing the catheter, the steps of:
providing the catheter with an inflatable means,
positioning the catheter such that the inflatable means is in the sphincter of Oddi,
inflating the inflatable means, and
holding the inflatable means in position for a period of time sufficient to achieve tamponade and dilate the sphincter of Oddi.

13. The method of claim 8 wherein the catheter is introduced to the common bile duct by passing the catheter through a laparoscopic port.

* * * * *